United States Patent
Wilson

(10) Patent No.: US 10,098,940 B2
(45) Date of Patent: Oct. 16, 2018

(54) EXOTOXIN/THERMOLYSIN COMPOSITIONS AND METHODS AND USES FOR TREATING OR PREVENTING LAMINITIS

(71) Applicant: University of Saskatchewan, Saskatoon (CA)

(72) Inventor: David G. Wilson, Saskatoon (CA)

(73) Assignee: University of Saskatchewan, Saskatoon, Saskatchewan (CA)

( * ) Notice: Subject to any disclaimer, the term of this patent is extended or adjusted under 35 U.S.C. 154(b) by 0 days.

(21) Appl. No.: 15/320,159

(22) PCT Filed: Jun. 19, 2015

(86) PCT No.: PCT/CA2015/000399
§ 371 (c)(1),
(2) Date: Dec. 19, 2016

(87) PCT Pub. No.: WO2015/192216
PCT Pub. Date: Dec. 23, 2015

(65) Prior Publication Data
US 2017/0136113 A1     May 18, 2017

Related U.S. Application Data

(60) Provisional application No. 62/014,989, filed on Jun. 20, 2014.

(51) Int. Cl.
*A61K 39/00* (2006.01)
*A61K 39/09* (2006.01)
*A61K 39/02* (2006.01)

(52) U.S. Cl.
CPC ............ *A61K 39/092* (2013.01); *A61K 39/02* (2013.01); *A61K 2039/552* (2013.01); *A61K 2039/57* (2013.01); *A61K 2039/58* (2013.01); *A61K 2039/70* (2013.01)

(58) Field of Classification Search
None
See application file for complete search history.

(56) References Cited

U.S. PATENT DOCUMENTS

| | | | |
|---|---|---|---|
| 5,641,492 A | 6/1997 | Sprouse et al. | |
| 6,287,555 B1 | 9/2001 | Gill et al. | |
| 7,011,826 B1 | 3/2006 | Rowe et al. | |
| 2003/0036644 A1* | 2/2003 | Ulrich | C07K 14/31 536/23.1 |
| 2006/0189791 A1 | 8/2006 | Winter et al. | |
| 2006/0292173 A1* | 12/2006 | MaCadam | C12N 1/20 424/203.1 |
| 2013/0315946 A1 | 11/2013 | Kuo et al. | |

FOREIGN PATENT DOCUMENTS

| | | | |
|---|---|---|---|
| EP | 0781340 B1 | 4/2005 | |
| WO | 96/08569 A2 | 3/1996 | |
| WO | 96/28177 A1 | 9/1996 | |
| WO | WO 2013151595 A1 * | 10/2013 | ............. A61K 39/39 |

OTHER PUBLICATIONS

Cruse et al., Illustrated Dict. of Immunology, 2nd ed., CRC Press, 2003, p. 46.*
McGuinness et al. (Mol. Microbiol., 7:505-514, 1993).*
Moudallal et al. (EMBO Journal, 1:1005-1010, 1982).*
Abaza et al. (J. Prot. Chem., 11:433-444, 1992).*
Sudheesh, P.S. et al., "Identification of potential vaccine target antigens by immunoproteomic analysis of a virulent and a non-virulent strain of the fish pathogen *Flavobacterium psychrophilum*", Dis Aquat Organ, Feb. 8, 2007, vol. 74, pp. 37-47.
Mungall, B.A. et al., "In vitro evidence for a bacterial pathogenesis of equine laminitis", Vet Microbiol, Apr. 2, 2001, vol. 79, pp. 209-223.
Kapur, V. et al., "Vaccination with streptococcal extracellular cysteine protease (interleukin-1β convertase) protects mice against challenge with heterologous group A *Streptococci*", Microb Pathog, Jun. 1994, vol. 16, No. 6, pp. 443-450.
Kapur, V. et al., "A conserved *Streptococcus pyogenes* extracellular cysteine protease cleaves human fibronectin and degrades vitronectin", Microb Pathog, Nov. 1993, vol. 15, pp. 327-346.
Hytonen, H. et al., "The SpeB virulence factor of *Streptococcus pyogenes*, a multifunctional secreted and cell surface molecule with strepadhesin, laminin-binding and cysteine protease activity", Molecular Microbiology, 2001, vol. 39, No. 2, pp. 512-519.
Morefield, Garry, et al. "Development of a Recombinant Fusion Protein Vaccine Formulation to Protect against *Streptococcus pyogenes*." Vaccine, vol. 32, No. 30, 2014, pp. 3810-3815.
Ulrich, Robert G. "Vaccine Based on a Ubiquitous Cysteinyl Protease and Streptococcal Pyrogenic Exotoxin A Protects against *Streptococcus pyogenes* Sepsis and Toxic Shock." Journal of Immune Based Therapies and Vaccines, vol. 6, No. 1, 2008, p. 8.
Lucchese, Guglielmo et al. "How a Single Amino Acid Change May Alter the Immunological Information of a Peptide." Frontiers in Bioscience, vol. E4, No. 5, 2012, pp. 1843-1852.

* cited by examiner

*Primary Examiner* — Brian Gangle
(74) *Attorney, Agent, or Firm* — Bereskin & Parr LLP; Melanie Szweras

(57) ABSTRACT

The disclosure relates to immunogenic and vaccine compositions comprising *Streptococcus* exotoxins and/or bacterial thermolysins from M4 protease family. Also provided are kits, methods and uses of said compositions for treating or preventing laminitis in a hooved animal.

6 Claims, No Drawings

EXOTOXIN/THERMOLYSIN COMPOSITIONS AND METHODS AND USES FOR TREATING OR PREVENTING LAMINITIS

RELATED APPLICATIONS

This application is a national phase entry of PCT/CA2015/000399 filed Jun. 19, 2015 (which designates the U.S.), which claims the benefit of priority to U.S. Provisional application No. 62/014,989 filed Jun. 20, 2014 (now expired), the contents of both of which are incorporated herein by reference in their entirety.

FIELD

The present disclosure relates to compositions comprising *Streptococcus* exotoxins and/or bacterial thermolysins from the M4 protease family and methods and uses thereof for treating or preventing laminitis.

BACKGROUND

Laminitis is a common and often life-threatening condition in the horse. The condition is either at the top or within the top three priorities for every major funding agency in North America. Irrespective of the initiating cause, the end result is mechanical failure of the hoof due to varying degrees of separation of the insensitive part of the hoof from the underlying sensitive tissues. For over three decades, North American researchers have focused on unraveling a complex series of vascular events believing a state of under-perfusion exists during the development of the disease. Interestingly, these vascular events do not develop until after the onset of clinical lameness leaving many to question whether they are simply a response to the mechanical disruption of the hoof, rather than a cause of the condition. In fact, a recent report shows an increase in sub-laminar blood flow during the prodomal stages of experimentally induced laminitis (Pollitt et al., 1998).

Laminitis can be induced using a carbohydrate over-ingestion (CHO) model (Garner et al., 1975) and pre-treatment with virginiamycin will prevent the development of clinical laminitis suggesting microbial involvement in the development of the disease (Rowe et al., 1994). The original CHO model is associated with unacceptable incidences of colic and mortality and has been replaced with an oligofructose model (Pollitt et al., 2003). Using this model, an overgrowth of *Streptococcus* species in the hindgut has been demonstrated (Milinovich et al., 2006). Ex vivo studies of the hoof have confirmed that matrix metalloproteinases (MMP) 2 and 9 are activated when hoof explants are exposed to the *Streptococcus bovis* exotoxin. The cysteine protease, *Streptococcus* pyrogenic exotoxin B (SpeB), also had a direct effect on the tissue. Both treatments resulted in dissolution of the basement membrane and separation of the hoof wall proper from the underlying sensitive tissues when mechanical traction is applied across the lamina (Mungall et al., 2001). The basement membrane failure is believed to result from the cleavage of the protein laminin which is an essential component of the cytoskeletal system that suspends the coffin bone within the hoof proper (French et al., 2004). Histologically, the lesion is identical to that observed in clinical manifestations of the condition (Mungall et al., 2001).

It is known that exposure of hoof explants to *Streptococcus* exotoxins results in local activation of MMPs and that MMPs are up-regulated in hoof explants from clinically affected horses. However, it is not known whether this up-regulation is limited to the foot or whether exotoxin is present in the hoof of clinically affected horses.

There is considerable evidence supporting a bacterial contribution in the pathogenesis of laminitis (Rowe et al., 1994; Milinovich et al., 2006; Mungall et al., 2001). Studies in mice and rabbits have shown antibodies to SpeB effectively inhibit protease activity and improve survival of mice challenged with intraperitoneal injections of *Streptococcus pyogenes* (Kapur et al. 1994). *Streptococcus* exotoxins SpeB and bacterial M4 family thermolysins are highly conserved (Kapur et all 1993; Adekoya and Sylte, 2009) and have been implicated in the development of laminitis (Mungall et al., 2001). Continuous cryotherapy is well tolerated and can effectively limit the hoof damage associated with the development of laminitis in horses undergoing oligofructose induced laminitis (Kapur et al., 1994; Kapur et al., 1993; Pollitt et al., 2004; van Eps et al., 2004). The observed protective effect may be a result of reduced delivery of laminitis "trigger factors" or possibly related to expected reduction of enzymatic activities due to reduced temperature (van Eps et al., 2009a). Irrespective of the mode of protection, clinical laminitis can be prevented by standing horses in knee deep ice-water for 72 hours during the oligofructose induction protocol. Furthermore, any histologic remnants of acute laminitis resolve within 7 days (van Eps et al., 2009b).

The primary focus of Streptococcal immunoprophylaxis has been M protein. Unfortunately, there is extensive variation between serotypes and concern that autoimmune responses can occur. Vaccination of mice against SpeB reduced morbitity and mortality due to a streptococcal infection model (Kapur et al. 1994). Antibodies raised against the 40 kDa precursor form of SpeB were not as effective as those raised against the 28 kDa cleaved form (Matsuka et al. 1999).

Mungall et al. (2001) discloses a possible link between laminitis and bacterial proteins, including thermolysin and SpeB. Mungall et al. further discloses that *Streptococcus bovis* is a key bacterium responsible for fermenting starch in the equine hindgut.

Sudheesh et al. (2007) discloses that the thermolysin protein of *Flavobacterium psychrophilum* is antigenic and that this protein may be used for targeted vaccine development against bacterial coldwater disease and rainbow trout fry syndrome in fish.

European Patent No. EP 0781340 discloses a vaccine against a Streptococcal exotoxin B (SpeB) protein comprising at least one amino acid substitution at Cys192 or His340, which disrupts cysteine protease activity. The vaccine was produced by inoculating mice with purified SpeB subcutaneously followed by intraperitoneal boost.

WO/1996/008569 discloses a vaccine against a Streptococcal (specifically *S. pyogenes*) extracellular cysteine protease (SpeB), or a fragment thereof.

U.S. Pat. No. 6,287,555 discloses a vaccine against *Streptococcus bovis*, using live cells, attenuated cells, killed whole cells, or cell lysate as an inoculant, for the purpose of protecting animals, including horses, from the effects of overproduction of acid and further discloses that overproduction of acid causes a variety of conditions, including laminitis.

U.S. Pat. No. 7,011,826 discloses the use of a vaccine comprising a live or dead *Streptococcus* strain, selected from specific *Streptococcus* strains including *S. bovis* SbR1 and *S.*

*equinus* SER1, to protect against acidosis and further discloses that acid accumulation in the gut can result in laminitis in horses.

U.S. Pat. No. 5,641,492 discloses a vaccine for protecting horses and cattle against endotoxin-associated diseases, including laminitis. The vaccine comprises a killed suspension of a bacterial mutant, particularly a *Salmonella* mutant, which lacks an 0-carbohydrate side chain.

SUMMARY

The present inventor has shown that natural exposure to laminitis results in protection from a subsequent challenge. The present inventor has further shown that exposure of horses to *Streptococcus* exotoxins, SpeB and/or *Geobacillus stearothermophilus* protease, thermolysin, are sufficient to induce an immune response and to provide protection against laminitis challenge.

Accordingly, in one aspect, provided herein is an immunogenic composition comprising a bacterial thermolysin from the M4 protease family or a variant thereof and/or one or more forms of a *Streptococcus* pyrogenic exotoxin B (SpeB) or variants thereof. In an embodiment, the immunogenic composition comprises a bacterial thermolysin from the M4 protease family or a variant thereof. In another embodiment, the immunogenic composition comprises one or more forms of an SpeB or a variant thereof. In yet another embodiment, the immunogenic composition comprises a bacterial thermolysin from the M4 protease family or a variant thereof and one or more forms of a SpeB or variants thereof.

In an embodiment, the immunogenic composition disclosed herein further comprises a pharmaceutically acceptable excipient, carrier, buffer, stabilizer, or mixtures thereof.

In an embodiment, the bacterial thermolysin from the M4 protease family is a thermolysin from *Geobacillus, Bacillus, Pseudomonas, Streptococcus, Lactobacillus, Enterococcus, Leuconstoccus* and *Carnobacteria*. In one embodiment, the thermolysin is from *Geobacillus* or *Bacillus*, optionally *Bacillus thermoproteolyticus* or *Geobacillus stearothermophilus*.

In an embodiment, the one or more forms of SpeB comprises a 40 kDa precursor form and/or a 28 kDa cleaved form. Optionally, the one or more forms of SpeB are from *Streptococcus pyogenes*.

In an embodiment, the immunogenic composition further comprises an immunostimulatory component, such as an adjuvant. Optionally the adjuvant is an oil/water based adjuvant, such as EMULSIGEN™-D. Other adjuvants include, without limitation, saponins, squalene, carbomer, alum, iscoms, CpG, emulsions, microparticles, liposomes, and cholera toxin.

In another aspect, there is provided a vaccine composition comprising a bacterial thermolysin from the M4 protease family or a variant thereof and/or one or more forms of a *Streptococcus* pyrogenic exotoxin B (SpeB) or variants thereof. In an embodiment, the vaccine composition comprises a bacterial thermolysin from the M4 protease family or a variant thereof. In another embodiment, the vaccine composition comprises an SpeB or a variant thereof. In yet another embodiment, the vaccine composition comprises a bacterial thermolysin from the M4 protease family or a variant thereof and one or more forms of a SpeB or variants thereof.

In an embodiment, the vaccine composition disclosed herein further comprises a pharmaceutically acceptable excipient, carrier, buffer, stabilizer, or mixtures thereof.

In an embodiment, the bacterial thermolysin from the M4 protease family is a thermolysin from *Geobacillus, Pseudomonas, Streptococcus, Bacillus, Lactobacillus, Enterococcus, Leuconstoccus* and *Carnobacteria*. In one embodiment, the thermolysin is from *Geobacillus* or *Bacillus*, optionally *Bacillus thermoproteolyticus* or *Geobacillus stearothermophilus*.

In an embodiment, the one or more forms of SpeB comprises a 40 kDa precursor form and/or a 28 kDa cleaved form. Optionally, the one or more forms of SpeB are from *Streptococcus pyogenes*.

In an embodiment, the vaccine composition disclosed herein further comprises an immunostimulatory component, such as an adjuvant. Optionally the adjuvant is an oil/water based adjuvant, such as EMULSIGEN™-D. In another embodiment, the adjuvant is saponins, squalene, carbomer, alum, iscoms, CpG, emulsions, microparticles, liposomes, and cholera toxin.

In yet another aspect, there is provided a kit comprising an immunogenic composition or a vaccine composition disclosed herein and instructions for the use thereof.

Another aspect of the present disclosure is a method of inducing an immune response in a hooved animal, comprising administering to said animal an effective amount of an immunogenic composition or a vaccine composition disclosed herein. Also provided herein is a use of an immunogenic composition or a vaccine composition disclosed herein for inducing an immune response in a hooved animal. Further provided is a use of an immunogenic composition or a vaccine composition disclosed herein in the preparation of a medicament for inducing an immune response in a hooved animal. Even further provided is an immunogenic composition or a vaccine composition disclosed herein for use in inducing an immune response in a hooved animal.

A further aspect of the present disclosure is a method of treating or preventing laminitis in a hooved animal, comprising administering to said animal an effective amount of an immunogenic composition or a vaccine composition disclosed herein. Also provided herein is a use of an immunogenic composition or a vaccine composition disclosed herein for treating or preventing laminitis in a hooved animal. Further provided is a use of an immunogenic composition or a vaccine composition disclosed herein in the preparation of a medicament for treating or preventing laminitis in a hooved animal. Even further provided is an immunogenic composition or a vaccine composition disclosed herein for use in treating or preventing laminitis in a hooved animal.

In one embodiment, the hooved animal is a horse. In another embodiment, the hooved animal is a cow.

Other features and advantages of the present disclosure will become apparent from the following detailed description. It should be understood, however, that the detailed description and the specific examples while indicating embodiments of the disclosure are given by way of illustration only, since various changes and modifications within the spirit and scope of the disclosure will become apparent to those skilled in the art from this detailed description.

DETAILED DESCRIPTION

Definitions

As used herein the term "immunogenic" means the ability to elicit an immune response.

As used herein the term "vaccine for treating or preventing laminitis" refers to a composition that prevents or reduces the severity of laminitis.

The term "therapeutically effective amount", "effective amount" or "sufficient amount" means a quantity sufficient to, when administered to the hooved animal, including a horse, achieve a desired result, for example an amount effective to elicit an immune response in a hooved animal. Effective amounts of therapeutic may vary according to factors such as the disease state, age, sex, weight of the animal. Dosage or treatment regime may be adjusted to provide the optimum therapeutic response.

The expression "biologically compatible form in vivo" as used herein means a form of the substance to be administered in which any toxic effects are outweighed by the therapeutic effects.

The term "eliciting an immune response" or "inducing an immune response" as used herein means initiating, triggering, causing, enhancing, improving or augmenting any response of the immune system, for example, of either a humoral or cell-mediated nature. The initiation or enhancement of an immune response can be assessed using assays known to those skilled in the art including, but not limited to, antibody assays (for example ELISA assays), antigen specific cytotoxicity assays and the production of cytokines (for example ELISPOT assays).

The term "hooved animal" as used herein refers to any member of the group of large mammals having hooves, also known as ungulates. In an embodiment, the hooved animal is a horse or a cow. Optionally, the hooved animal is a horse.

As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

"Palliating" a disease or disorder means that the extent and/or undesirable clinical manifestations of a disorder or a disease state are lessened and/or time course of the progression is slowed or lengthened, as compared to not treating the disorder.

For example, the phrase "treating or preventing laminitis" includes preventing laminitis altogether, decreasing the severity of laminitis or improving signs and symptoms related to laminitis. Signs and symptoms of laminitis include, without limitation, difficulty in walking and turning, standing awkwardly with more weight on hind legs, while shifting weight from one foot to the other, warm hooves with increased digital artery pulse rate; and depression at the coronary band.

The term "M4 protease family" as used herein refers to a family of proteases that have the HEXXH zinc-binding motif in one of the distinctive six-strand beta sheet with two helices in the N-terminal domain. The C-terminal domain, which is unique for the family, is predominantly helical and carries the third zinc ligand. M4 proteases are often called thermolysins. Most members of the family are secreted enzymes that degrade extracellular proteins and peptides for bacterial nutrition.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

Compounds and Compositions

The present disclosure includes an immunogenic composition or a vaccine composition comprising a bacterial thermolysin from the M4 protease family or a variant thereof and/or one or more forms of a *Streptococcus* pyrogenic exotoxin B (SpeB) or variants thereof. In an embodiment, the immunogenic composition or vaccine composition comprises a bacterial thermolysin from the M4 protease family or a variant thereof. In another embodiment, the immunogenic composition or vaccine composition comprises one or more forms of an SpeB or a variant thereof. In yet another embodiment, the immunogenic composition or vaccine composition comprises a bacterial thermolysin from the M4 protease family or a variant thereof and one or more forms of a SpeB or variants thereof.

In an embodiment, the vaccine composition disclosed herein further comprises a pharmaceutically acceptable excipient, carrier, buffer, stabilizer, or mixtures thereof.

In an embodiment, the bacterial thermolysin from the M4 protease family is a thermolysin from *Geobacillus, Pseudomonas, Streptococcus, Bacillus, Lactobacillus, Enterococcus, Leuconstoccus* and *Carnobacteria*. In one embodiment, the thermolysin is from *Geobacillus* or *Bacillus*, optionally *Bacillus thermoproteolyticus* or *Geobacillus stearothermophilus*.

In an embodiment, the one or more forms of SpeB comprises a 40 kDa precursor form and/or a 28 kDa cleaved form. Optionally, the one or more forms of SpeB are from *Streptococcus pyogenes*.

The term "SpeB" as used herein refers to the Streptococcal cysteine protease (streptopain) or streptococcal pyrogenic exotoxin B from any organism or source. For example, SpeB from *Streptococcus pyogenes NZ*131 has been deposited as Genbank Accession No. NC_011375.1; SpeB from *Streptococcus pyogenes* MGAS6180 has been deposited as Genbank Accession No. NC_007296.1; SpeB from *Streptococcus pyogenes* M1GAS has been deposited as Genbank Accession No. NC_002737.1.

The term "bacterial thermolysin from the M4 protease family" as used herein refers to a member of the M4 protease family from any bacterial organism or source. For example, thermolysins are found in a number of bacteria, including without limitation, *Geobacillus, Pseudomonas, Streptococcus Bacillus, Lactobacillus, Enterococcus, Leuconstoccus* and *Carnobacteria*. In one embodiment, the thermolysin is from *Geobacillus* or *Bacillus*, optionally *Bacillus thermoproteolyticus* or *Geobacillus stearothermophilus*. Sequences of thermolysins are known to a person skilled in the art. For example, thermolysin from *B. thermoproteolyticus* has been deposited as Genbank Accession Nos. X76986.1, A20191.1, AR106099, AR106098.1, A45713.1 and A45712.1.

Within the context of the present specification, the isolated *Streptococcus* exotoxin and thermolysin polypeptides of the disclosure may in one embodiment include various structural forms of the primary protein. For example, a polypeptide of the disclosure may be in the form of acidic or basic salts or in neutral form. In addition, individual amino acid residues may be modified by oxidation or reduction.

The term "isolated" as used herein refers to a polypeptide substantially free of cellular material or culture medium when produced by recombinant DNA techniques—i.e., a recombinant polypeptide—or chemical precursors, or other chemicals when chemically synthesized—i.e., a synthetic polypeptide.

In addition to the full-length polypeptides, thermolysin, 40 kDa SpeB and 28 kDa SpeB, polypeptides of the present disclosure may also include variants, such as truncations of the polypeptide, analogs, and homologues of the proteins, including truncations thereof, as described herein.

The term "variant" as used herein refers to an altered version of an exotoxin or thermolysin disclosed herein, wherein the altered version retains a significant ability to elicit an immune response, as would be readily understood by a person skilled in the art. Possible polypeptide alterations can include any one or more of those described herein. For example, an SpeB variant may comprise at least one amino acid substitution at Cys192 or His340, which disrupts cysteine protease activity but is still able to elicit an immune response.

Analogs of the exotoxin or thermolysin polypeptides described herein, may include, but are not limited to an amino acid sequence containing one or more amino acid substitutions, insertions, and/or deletions. Amino acid substitutions may be of a conserved or non-conserved nature. Conserved amino acid substitutions involve replacing one or more amino acids of the proteins of the disclosure with amino acids of similar charge, size, and/or hydrophobicity characteristics.

One or more amino acid insertions may be introduced into the amino acid sequence of an exotoxin or thermolysin polypeptide disclosed herein. Amino acid insertions may consist of single amino acid residues or sequential amino acids ranging from 2 to 15 amino acids in length.

Deletions may consist of the removal of one or more amino acids, or discrete portions from the amino acid sequence of an exotoxin or thermolysin polypeptide disclosed herein. The deleted amino acids may or may not be contiguous.

Exemplary methods of making the alterations set forth above are disclosed by Sambrook et al (Molecular Cloning: A Laboratory Manual, 2nd Ed., Cold Spring Harbor Laboratory Press, 1989).

A homologous protein includes a protein with an amino acid sequence having at least 60%, at least 70%, at least 75%, at least 80%, at least 85%, at least 90%, at least 95% or at least 98% identity with the amino acid sequence of an exotoxin or thermolysin polypeptide disclosed herein.

The polypeptides described above (including truncations, analogs, etc.) may be prepared using recombinant DNA methods. In general, such methods are well understood by those of skill in the art and may comprise the steps of introducing into a host cell any recombinant nucleic acid that encodes the polypeptide, allowing the polypeptide to be expressed in the host cell and isolating and purifying the polypeptide. The polypeptides may be purified and/or isolated to various degrees using any one of a number of techniques known in the art.

Alternatively, the polypeptides or parts thereof can be prepared by chemical synthesis using techniques well known in the chemistry of proteins such as solid phase synthesis or synthesis in homogeneous solution.

The immunogenicity of the compositions disclosed herein can be significantly improved if the immunizing agent (i.e. the immunogenic compositions or vaccine compositions comprising the *Streptococcus* exotoxin and/or bacterial thermolysin) is regardless of administration format, co-immunized with an immunostimulatory component, such as an adjuvant. Adjuvants enhance the immunogenicity of an immunogen but are not necessarily immunogenic in of themselves. Adjuvants may act by retaining the immunogen locally near the site of administration to produce a depot effect facilitating a slow, sustained release of immunogen to cells of the immune system. Adjuvants can also attract cells of the immune system to an immunogen depot and stimulate such cells to elicit immune response. As such, embodiments of this present disclosure encompass compositions including for example immunogenic or vaccine or compositions further comprising adjuvants.

Accordingly, another aspect of the present disclosure is an immunogenic composition or a vaccine composition disclosed herein and an immunostimulatory component, such as an adjuvant. In one embodiment, the adjuvant is an oil/water based adjuvant, optionally EMULSIGEN™-D. Other adjuvants include, without limitation, saponins, squalene, carbomer, alum, iscoms, CpG, emulsions, microparticles, liposomes, and cholera toxin.

Adjuvants have been used for many years to improve the host immune responses to, for example, vaccines. Intrinsic adjuvants (such as lipopolysaccharides) normally are the components of killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects making them unsuitable for use in animals. Indeed, only aluminum hydroxide and aluminum phosphate (collectively commonly referred to as alum) are routinely used as adjuvants in veterinary vaccines. The efficacy of alum in increasing antibody responses to Diphtheria and Tetanus toxoids is well established.

A wide range of extrinsic adjuvants can provoke potent immune responses to immunogens. These include saponins complexed to membrane protein antigens (immune stimulating complexes), pluronic polymers with mineral oil, killed mycobacteria and mineral oil, Freund's complete adjuvant, bacterial products such as muramyl dipeptide (MDP) and lipopolysaccharide (LPS), as well as lipid A, and liposomes.

In one aspect of the present disclosure, adjuvants useful in any of the embodiments described herein are as follows. Adjuvants for parenteral immunization include aluminum compounds (such as aluminum hydroxide, aluminum phosphate, and aluminum hydroxy phosphate). The antigen can be precipitated with, or adsorbed onto, the aluminum compound according to standard protocols. Other adjuvants such as RIBI (ImmunoChem, Hamilton, Mont.) can also be used in parenteral administration.

Adjuvants for mucosal immunization include bacterial toxins (e.g., the cholera toxin (CT), the *E. coli* heat-labile toxin (LT), the *Clostridium difficile* toxin A and the pertussis toxin (PT), or combinations, subunits, toxoids, or mutants thereof). For example, a purified preparation of native cholera toxin subunit B (CTB) can be of use. Fragments, homologs, derivatives, and fusion to any of these toxins are also suitable, provided that they retain adjuvant activity. Optionally, a mutant having reduced toxicity is used. Suitable mutants have been described (e.g., in WO 95/17211 (Arg-7-Lys CT mutant), WO 96/6627 (Arg-192-Gly LT mutant), and WO 95/34323 (Arg-9-Lys and Glu-129-Gly PT mutant)). Additional LT mutants that can be used in the methods and compositions disclosed herein include, for example Ser-63-Lys, Ala-69-Gly, Glu-110-Asp, and Glu-112-Asp mutants. Other adjuvants (such as a bacterial monophosphoryl lipid A (MPLA) of various sources (e.g., *E. coli*, *Salmonella minnesota*, *Salmonella typhimurium*, or *Shigella flexneri*, saponins, or polylactide glycolide (PLGA) microspheres) can also be used in mucosal administration.

Adjuvants useful for both mucosal and parenteral immunization include polyphosphazene (for example, WO 95/2415), DC-chol (3 b-(N-(N',N'-dimethyl aminomethane)-carbamoyl) cholesterol (for example, U.S. Pat. No. 5,283,185 and WO 96/14831) and QS-21 (for example, WO 88/9336).

Another aspect of the present disclosure is a kit comprising the immunogenic compositions disclosed herein or the vaccine compositions disclosed herein, and instructions for use thereof.

The kit can also include ancillary agents. For example, the kit can include an instrument for injecting the immunogenic composition of the present disclosure into an animal, such as a syringe; a vessel for storing or transporting the immunogenic composition; and/or pharmaceutically acceptable excipients, carriers, buffers or stabilizers.

Methods and Uses

Another aspect of the present disclosure is a method of inducing an immune response in a hooved animal, comprising administering to said animal an effective amount of an immunogenic composition or a vaccine composition disclosed herein. Also provided herein is a use of an immunogenic composition or a vaccine composition disclosed herein for inducing an immune response in a hooved animal. Further provided is a use of an immunogenic composition or a vaccine composition disclosed herein in the preparation of a medicament for inducing an immune response in a hooved animal. Even further provided is an immunogenic composition or a vaccine composition disclosed herein for use in inducing an immune response in a hooved animal.

A further aspect of the present disclosure is a method of treating or preventing laminitis comprising administering the immunogenic composition or vaccine composition disclosed herein to a hooved animal in need thereof. Also provided herein is a use of an immunogenic composition or a vaccine composition disclosed herein for treating or preventing laminitis in a hooved animal. Further provided is a use of an immunogenic composition or a vaccine composition disclosed herein in the preparation of a medicament for treating or preventing laminitis in a hooved animal. Even further provided is an immunogenic composition or a vaccine composition disclosed herein for use in treating or preventing laminitis in a hooved animal.

An animal subject may be immunized with a composition including for example an immunogenic or vaccine composition comprising the *Streptococcus* exotoxins and/or bacterial thermolysins disclosed in the present disclosure by any conventional route as is known to one skilled in the art. This may include, for example, immunization via a mucosal (e.g., ocular, intranasal, oral, gastric, pulmonary, intestinal, rectal, vaginal, or urinary tract) surface, via the parenteral (e.g., subcutaneous, intradermal, intramuscular, intravenous, or intraperitoneal) route or intranodally. Preferred routes depend upon the choice of the immunogen as will be apparent to one skilled in the art. The administration can be achieved in a single dose or repeated at intervals. The appropriate dosage depends on various parameters understood by skilled artisans such as the immunogen itself (i.e. peptide vs. nucleic acid (and more specifically type thereof), the route of administration and the condition of the animal to be vaccinated (weight, age and the like).

The *Streptococcus* exotoxins, bacterial thermolysins, or immunogenic compositions or vaccine compositions described herein can be prepared by per se known methods for the preparation of pharmaceutically acceptable compositions that can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, 20th ed., Mack Publishing Company, Easton, Pa., USA, 2000). On this basis, the compositions include, albeit not exclusively, solutions of the substances in association with one or more pharmaceutically acceptable vehicles or diluents, and contained in buffered solutions with a suitable pH and iso-osmotic with the physiological fluids.

Compositions including for example immunogenic or vaccine compositions of the present disclosure may comprise a pharmaceutically acceptable carrier. Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, ethanol, N-(1(2,3-dioleyloxy) propyl)N,N,N-trimethylammonium chloride (DOTMA), diolesylphosphotidyl-ethanolamine (DOPE), and liposomes. Such compositions should contain a therapeutically effective amount of the compound, together with a suitable amount of carrier so as to provide the form for direct administration to the animal.

The composition may be in the form of a pharmaceutically acceptable salt which includes, without limitation, those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylarnino ethanol, histidine, procaine, etc.

The methods and uses of the present disclosure are applicable to hooved animals including for example, horses or cows.

The above generally describes the present disclosure. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1

Natural Exposure to Laminitis Prevents Subsequent Laminitis

The present inventor hypothesized that *Streptococcus* exotoxins and bacterial thermolysins from M4 protease family released from the intestinal tract during induction of laminitis would result in autovaccination. Laminitic horses seem predisposed to recurrences; however, secondary episodes may be related to physical disruption of the hoof and associated complications, rather than a new assault on the basement membrane. A second attempt to induce laminitis in horses where the initial laminar insult has been tempered by cryotherapy allows assessment of possible immunity as a result of natural exposure.

Materials and Methods

Four adult horses were pre-conditioned in the animal care unit for 3 weeks during which time they were fed free choice grass-alfalfa hay. Laminitis was induced using the oligofructose model of van Epp and Pollitt (90% of horses develop laminitis) (vanEps, 2006). Horses received 10 g/kg of oligofructose (time 0). Horses were confined in custom fabricated stocks that allowed horses to continuously stand knee deep in ice water for a period of 72 hours (time 72). Horses were not expected to develop lameness; (vanEps, 2004, vanEps, 2009) however, any horse that developed Obel grade 2 lameness was euthanized using a barbiturate overdose and hoof tissue examined histologically for the presence of lesions consistent with laminitis (Pollitt, 1996).

After the 8 week period, a second attempt was made to induce laminitis without the benefit of cryotherapy using the same oligofructose model as described above. Horses that developed Obel grade 2 laminitis would be euthanized using a barbiturate overdose and hoof tissue would be examined histologically for the presence of lesions typical of laminitis (Pollitt 1996).

Results:

None of the 4 horses developed lameness (laminitis) during the initial oligofructose challenge accompanied by 72 hours of continuous cryotherapy. Subsequent oligofructose challenge 8 weeks in absence of cryotherapy did not result in clinically laminitis. It was also demonstrated that natural exposure through the oligofructose induction model while utilizing continuous cryotherapy induced protection against subsequent induction model challenge. One horse was challenged twice and did not develop laminitis during either challenge.

Example 2

*Steptococcus* Exotoxin/*Geobacillus* Thermolysin Exposure Induces Antibodies in Horses Study #1

Materials and Methods

A trivalent vaccine was made using 30 pg each of thermolysin (*Geobacillus* thermolysin from Sigma), SpeB 40 kDa and SpeB 28 kDa in 30% EMULSIGEN™-D. Two ml of vaccine was administered at 3 week intervals. Antibody titres were measured before vaccination and at 3, 6 and 9 week post-vaccination.

Four weeks after the last vaccination, horses were subjected to the oligofructose model to attempt to induce laminitis.

Results

Increases in titres in horses injected with the trivalent composition clearly indicated a response to the vaccine (Table 1). Four weeks after the last vaccination, the horses were subjected to the oligofructose induction model. All of the 15 horses developed depression and severe gastrointestinal upset; however, only 3 of 15 horses developed lameness indicating a protective effect in 80% of the horses. The oligofructose laminitis induction model is almost 100 percent successful in inducing severe lameness. For humane reasons, control horses were not included in the initial vaccine trial.

Example 3

*Streptococcus* Exotoxin/*Geobacillus* Thermolysin Exposure-Study #2

Materials and Methods

Twenty mixed breed horses over 2 years of age were purchased from a local dealer. Horses were randomly assigned to a control group (10 horses) and a vaccinate group (10 horses). Vaccinated horses each received 3 doses a trivalent vaccine comprised of 30 ug each of thermolysin, SpeB 40kDa (mutant type) and 28 kDa SpeB (wild type) in Emulsigen® subcutaneously at 21 day intervals. All horses were randomly assigned to be challenged using the oligofructose carbohydrate overload model 3 weeks after the final vaccine booster. Challenged horses were observed for lameness by a clinician blinded to the treatment. Any horse that developed Obel grade 3 lameness was euthanized and tissue was collected from the feet for attempts at detection of Streptococcal exotoxin in the laminar tissue at a later date.

Serum was collected from vaccinated horses before the initial vaccination, at the time of each subsequent vaccination and 3 weeks after the final booster. Serum was collected from control horses at day 0 and 9 weeks later (coincided with final collection in vaccinated horses). Serum titres for antibodies to thermolysin, SpeB 40kDa (precursor) and 28 kDa SpeB (cleaved) were determined at each time frame.

Results

Ten randomly selected horses were challenged (5 controls and 5 vaccinates). All 5 control horses developed Obel grade 3 lameness within 18 -24 hours of oligofructose administration. One vaccinated horse was Obel grade 1 lame at 24 hours but the lameness resolved with a single dose of phenylbutazone (4.4 mg/kg, per os). Given the consistency of the oligofructose overload model in the initial 5 control horses, the remaining 5 control horses were not challenged owing to animal welfare considerations. Four additional vaccinated horses were challenged and only one horse developed Obel grade 1 lameness that resolved untreated within 24 hours. The $10^{th}$ vaccinated horse delivered a foal a week before her oligofructose challenge date and was removed from the study.

Similar to the preceeding 15 horse vaccination trial, all vaccinates developed a significant immune response (Table 2).

Discussion:

The most common cause of laminitis in horses is gastrointestinal upset. Without wishing to be bound by theory, this study shows that overgrowth of bacterial species in the hindgut results in increased absorption of *Streptococcal* exotoxin and bacterial thermolysin which causes dissolution of the laminar basement membrane in the hoof resulting in mechanical failure of the hoof. This study demonstrated that an immune response can be generated by vaccinating horses with these exotoxins/thermolysins. Challenge of vaccinated horses has shown an 80% efficacy.

Example 4

Independent Exposure to *Streptococcus* Exotoxin or *Geobacillus* Thermolysin Materials and Methods Twenty mixed breed horses over 2 years of age were purchased from a local dealer. Horses were randomly assigned to a thermolysin vaccination group (10 horses) and a SpeB vaccination group (10 horses). Horses were vaccinated subcutaneously with 3 doses of vaccine comprising 30 ug of either thermolysin or 28 kDa SpeB (wild type) in Emulsigen® at 21 day intervals. All horses were randomly assigned to be challenged using the oligofructose carbohydrate overload model 3 weeks after the final vaccine booster. Challenged horses were observed for lameness by a clinician blinded to the treatment.

Serum was collected from vaccinated horses before the initial vaccination and 3 weeks after the final booster. Serum titres for antibodies to thermolysin and 28 kDa SpeB (cleaved) may be determined at each time frame.

Results

SpeB Vaccination

Ten SpeB vaccinated horses were challenged using the oligofructose laminitis induction model as described above. Three horses became Obel grade 1 lame within 24 hours; however, their lameness had resolved without treatment by 72 hours post-induction. The remaining 7 horses displayed no signs of lameness. The vaccine was 70% effective in preventing the development of laminitis.

Thermolysis Vaccination

Nine thermolysin vaccinated horses were challenged using the oligofructose laminitis induction model as described above (One horse was not challenged because of difficult temperament). None of these horses developed any lameness, suggesting that the vaccine was 100% effective in this case.

While the present disclosure has been described with reference to what are presently considered to be the examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

Tables

TABLE 1

IgG Titers to Exotoxins Before and After Vaccination - Study #1

| Exotoxin/Thermolysin | IgG Titers | | | |
|---|---|---|---|---|
| | Pre-vaccination | 3 Weeks Post-Vaccination | 3 Weeks Post-Booster 1 | 3 Weeks Post-Booster 2 |
| 28 kDa SpeB Cleaved | 10,905 | 312,859 | 1,225,040 | 1,554,634 |
| 40 kDa SpeB Precursor | 22,189 | 297,052 | 1,759,465 | 1,902,842 |
| Thermolysin | 10,383 | 38,834 | 792,143 | 1,521,260 |

TABLE 2

IgG Titers to Exotoxins Before and After Randomized Vaccination Trial with Controls - Study #2

| Exotoxin/Thermolysin | IgG Titers Vaccinates | | | | IgG Titres Controls At Challenge (n-5) |
|---|---|---|---|---|---|
| | Pre-vaccination | 3 Weeks Post-Vaccination | 3 Weeks Post-Booster 1 | 3 Weeks Post-Booster 2 | |
| 28 kDa SpeB Cleaved | 14,312 (range; 283-60,820) | 19,650 (range; 4401-56,187) | 123,424 (range; 4823-255,343) | 544,215 (range; 27,336-1,653,436) | 73,304 (range; 8448-208,181) |
| 40 kDa SpeB Precursor | 30,313 (range; 459-275,640) | 250,448 (range; 15,843-1,388,837) | 2,125,390 (range; 322,288-2,634,995) | 1,150,614 (range; 3950-1,919,986) | 781,756 (range; 164-3,106,660) |
| Thermolysin | 8714 (range; 76-45,672) | 54,427 (range; 6639-147,481) | 982,023 (range; 185,492-2,256,092) | 345,468 (range; 1830-1,364,892) | 181,042 (range; 0-864,064) |

REFERENCES

Adekoya O A and Sylte I. The Thermolysin Family (M4) of Enzymes: Therapeutic and Biotechnological Potential. *Chemical Biology & Drug Design* 2009; 73: 7-16

French K R, Pollitt C C. Equine laminitis: cleavage of laminin 5 associated with basement membrane dysadhesion. *Equine Vet J* 2004; 36:242-247.

Garner H E, Coffman J R, Hahn A W, et al. Equine laminitis of alimentary origin: an experimental model. *Am J Vet Res* 1975; 36:441-449.

Kapur V, Topouzis S, Majesky M W, et al. A conserved *Streptococcus* pyogenes extracellular cysteine protease cleaves human fibronectin and degrades vitronectin. *Micro Path* 1993; 15:327-346.

Kapur V, Maffei J T, Greer R S, et al. Vaccination with streptococcal extracellular cysteine protease (interleukin-1β convertase) protects mice against challenge with heterologous group A streptococci. *Micro Path* 1994; 16:443-450.

Matsuka Y V, Pillai S, Gubb S, et al. Fibrinogen cleavage by the Steptococcus pyogenes extracellular cysteine protease and generation of antibodies that inhibit enzyme proteolytic activity. *Infect Immun* 1999; 67:4326-4333.

Milinovich G J, Trott, D J, Burell, et al. Changes in equine hindgut bacterial populations during oligofructose-induced laminitis. *Environ Micro* 2006; 8:885-898.

Mungall B A, Kyaw-Tanner M, Pollittt C C. In vitro evidence of a bacterial pathogenesis of equine laminitis. *Vet Micro* 2001; 79:209-223.

Pollitt C C. Basement membrane pathology: a feature of equine laminitis. *Equine Vet J* 1996; 28:38-46.

Pollitt C C, Davies C T. Equine laminitis: its development coincides with increased sublaminar blood flow. *Equine Vet J*, Suppl. 1998; 26:125-132.

Pollitt C C, Kyaw-Tanner M, French K R, et al. Equine laminitis. *Proc Am Assoc Eq Pract* 2003; 49:103-115.

Pollitt C C, van Eps A W. Prolonged, continuous distal limb cryotherapy in the horse. *Equine Vet J* 2004; 36:216-220.

Rowe J B, Lees D W, Dabney J M et al. Prevention of laminitis resulting from carbohydrate overload in horses. *Aust Equine Vet* 1994; 12:29.

Sudheesh P S, LaFrentz B R, Call D R, Siems W F, LaPatra S E, Wiens G D, Cain K D. Identification of potential vaccine target antigens by immunoproteomic analysis of a virulent and a non-virulent strain of the fish pathogen Flavobacterium psychrophilum. *Dis Aquat Organ.* 2007 Feb. 8;74(1):37-47.

van Eps A W, Pollitt C C. Equine laminitis: cryotherapy reduces the severity of acute lesions. *Equine Vet J* 2004; 36:255-260.

van Epps A W, Pollitt C C. Equine laminitis induced with oligofructose. Equine Vet J 2006; 38:203-208.

van Eps A W, Pollitt. Equine laminitis model: cryotherapy reduces the severity of lesions evaluated seven days after induction with oligofructose. *Equine Vet J* 2009(a); 41:741-746.

van Eps A W, Pollitt C C. Equine laminitis model: lamellar histopathology seven days after induction with oligofructose. *Equine Vet J* 2009(b); 41:735-740.

Zachariassen K E. Hypothermia and cellular physiology. *Arctic Med Res* 1991; 50 (Suppl 6):13-17.

The invention claimed is:

1. A method of inducing an immune response in a hooved animal, comprising administering to said animal an effective amount of an immunogenic composition comprising an isolated *Geobacillus* bacterial thermolysin and an isolated *Streptococcus* pyrogenic exotoxin B (SpeB), wherein the SpeB comprises a 40 kDa precursor form and/or a 28 kDa cleaved form.

2. A method of inducing an immune response in a hooved animal, comprising administering to said animal an effective amount of a vaccine composition comprising an isolated *Geobacillus* bacterial thermolysin and an isolated *Streptococcus* pyrogenic exotoxin B (SpeB), wherein the SpeB comprises a 40 kDa precursor form and/or a 28 kDa cleaved form.

3. A method of treating or preventing laminitis in a hooved animal comprising administering an immunogenic composition to the animal in need thereof, wherein the immunogenic composition comprises an isolated *Geobacillus* bacterial thermolysin and an isolated *Streptococcus* pyrogenic exotoxin B (SpeB), wherein the SpeB comprises a 40 kDa precursor form and/or a 28 kDa cleaved form.

4. The method of claim 1, wherein the hooved animal is a horse or cow.

5. The method of claim 4, wherein the hooved animal is a horse.

6. A method of treating or preventing laminitis in a hooved animal comprising administering a vaccine composition to the animal in need thereof, wherein the vaccine composition comprises an isolated *Geobacillus* bacterial thermolysin and an isolated *Streptococcus* pyrogenic exotoxin B (SpeB), wherein the SpeB comprises a 40 kDa precursor form and/or a 28 kDa cleaved form.

* * * * *